US010089442B2

(12) United States Patent
Van Zon et al.

(10) Patent No.: US 10,089,442 B2
(45) Date of Patent: Oct. 2, 2018

(54) EXECUTABLE GUIDELINE SOLUTION WITH MULTIPLE ALTERNATIVE VIEWS ON RECOMMENDED CARE STEPS

(71) Applicant: KONINKLIJKE PHILIPS N.V., Eindhoven (NL)

(72) Inventors: Cornelis Conradus Adrianus Maria Van Zon, Fishkill, NY (US); William Palmer Lord, Fishkill, NY (US)

(73) Assignee: Koninklijke Philips N.V., Eindhoven (NL)

( * ) Notice: Subject to any disclaimer, the term of this patent is extended or adjusted under 35 U.S.C. 154(b) by 379 days.

(21) Appl. No.: 14/383,979

(22) PCT Filed: Mar. 29, 2013

(86) PCT No.: PCT/IB2013/052547
§ 371 (c)(1),
(2) Date: Sep. 9, 2014

(87) PCT Pub. No.: WO2013/144918
PCT Pub. Date: Oct. 3, 2013

(65) Prior Publication Data
US 2015/0073818 A1    Mar. 12, 2015

Related U.S. Application Data

(60) Provisional application No. 61/617,415, filed on Mar. 29, 2012.

(51) Int. Cl.
*G06F 19/00* (2018.01)
*G16H 50/20* (2018.01)

(52) U.S. Cl.
CPC .......... *G06F 19/345* (2013.01); *G06F 19/325* (2013.01); *G16H 50/20* (2018.01)

(58) Field of Classification Search
CPC ........ G06Q 50/22; G06Q 10/10; G06Q 50/24; G06F 3/04842; G06F 17/212; G06F 19/345; G06F 19/325; H04L 65/601; G16H 50/20
See application file for complete search history.

(56) References Cited

U.S. PATENT DOCUMENTS 8,260,709 B2 *   9/2012   Holla .................... G06F 19/322
                                                         380/231
2003/0195988 A1  10/2003  Sahue et al.
(Continued)

FOREIGN PATENT DOCUMENTS

WO    2006087415 A1    8/2006
WO    2007054881 A2    5/2007
WO    2012023104 A1    2/2012

*Primary Examiner* — Maroun P Kanaan

(57) ABSTRACT

A system (10) for presenting guideline recommendations to care givers includes at least one display device (54, 56), each displaying a user interface. The system (10) further includes at least one processor (122, 118). The processor (122, 118) is programmed to receive a guideline recommendation for a patient based on a computer interpretable guideline (CIG) and present the guideline recommendation to at least one associated user according to a plurality of alternative approaches for representing the guideline recommendation. At least one of the plurality of alternative approaches uses the user interface of one of the at least one display device (54, 56) to represent the guideline recommendation.

20 Claims, 3 Drawing Sheets

(56) References Cited

U.S. PATENT DOCUMENTS

| | | |
|---|---|---|
| 2004/0012627 A1 | 1/2004 | Zakharia et al. |
| 2007/0214013 A1* | 9/2007 | Silverman ........... G06F 19/3431 705/2 |
| 2012/0150878 A1* | 6/2012 | Naeymi-Rad .......... G06Q 50/22 707/752 |

* cited by examiner

EXECUTABLE GUIDELINE SOLUTION WITH MULTIPLE ALTERNATIVE VIEWS ON RECOMMENDED CARE STEPS

CROSS-REFERENCE TO PRIOR APPLICATIONS

This application is the U.S. National Phase application under 35 U.S.C. § 371 of International Application No. PCT/IB2013/052547, filed on Mar. 29, 2013, which claims the benefit of U.S. Provisional Application No. 61/617,415, filed on Mar. 29, 2012. These applications are hereby incorporated by reference herein.

The present application relates generally to clinical decision making. It finds particular application in conjunction with clinical decision support systems and will be described with particular reference thereto. However, it is to be understood that it also finds application in other usage scenarios and is not necessarily limited to the aforementioned application.

Clinical guidelines (GLs) are recommendations on the appropriate treatment and care for people with specific diseases and conditions. The recommendations are typically based on the best available evidence. GLs consist of decisions and decision criteria for diagnosis, management, and treatment of patients with these specific diseases and conditions. Modern guidelines represent evidence-based medicine. In other words, they are based on clinical evidence acquired through scientific methods and studies, such as randomized clinical trials. Evidence-based practice is the foundation of modern guidelines and their application.

Studies have shown that adhering to the recommendations of clinical guidelines reduces costs of care and improves patient outcomes. As a result, guideline adherence is increasingly tied to performance measures and reimbursements. This creates an opportunity for healthcare solutions, in particular clinical decision support (CDS) systems, to support this trend. For such solutions to be successful, they have to fit seamlessly into existing clinical workflow. This can be achieved by representing clinical guidelines, and local care protocols that are derived from them, as computer interpretable guidelines (CIGs). CIGs are also known as executable clinical guidelines.

CIGs are computer interpretable representations of the clinical knowledge contained in guidelines. Software that can execute a CIG is typically referred to as a CIG engine. A CIG engine applies a CIG's logic to patient data and user input in order to generate recommendations for care providers. Hence, a CIG engine can execute computerized clinical guidelines and computerized local care protocols, where the latter may include workflow steps.

CIG engines can generate various types of output towards care providers, such as alerts ('High mortality risk detected'), notifications ('ACLS team required in room 2A'), messages ('Dr. Jones please call triage room, x8210'), and recommended care steps ('Perform CT scan of patient's head', 'Take vitals'). Generically, this output is referred to as guideline recommendations. Challenges with known CDS systems pertain to how the guideline recommendations get displayed to care givers.

Care givers have access to a wide variety of devices, such as pagers, smart phones, patient monitors, tablet PCs, mobile clinical assistants, laptops, workstations, and so on. These devices have varying screen real-estate, graphics capabilities, bandwidth, and processing power. With medical institutions being increasingly networked environments, it is increasingly desirable for CDS systems to work with a variety of devices. However, known CDS systems do not tailor the presentation of guideline recommendations to the specific devices.

Even more, the user interface of a CDS application, displayed on a good-size screen (e.g., a laptop screen or a workstation monitor), can have multiple, possibly resizable windows competing for screen real-estate. Known CDS systems do not tailor the presentation of guideline recommendations to the possibly varying window size.

Further, the user interface of a CDS application can consist of a wide variety of graphical and textual element types. The specific mix is catered to the type and nature of the application. Known CDS systems do not tailor the presentation of guideline recommendations to account for these variations in user interfaces.

Moreover, clincians may have to work under varying degrees of pressure. For example, a nurse in an emergency department may experience relative leisure in the absence of patients, but be under high pressure when several patients with severe conditions present at the same time. Known CDS systems do not tailor the presentation of guideline recommendations depending on the current working conditions.

The present application provides new and improved methods and systems which overcome the above-referenced challenges and others.

In accordance with one aspect, a system for presenting guideline recommendations to care givers is provided. The system includes at least one display device, each displaying a user interface, and at least one processor. The processor is programmed to receive a guideline recommendation for a patient based on a computer interpretable guideline (CIG) and present the guideline recommendation to at least one associated user according to a plurality of alternative approaches for representing the guideline recommendation. At least one of the plurality of alternative approaches use the user interface of one of the at least one display device to represent the guideline recommendation.

In accordance with another aspect, a method for presenting guideline recommendations to care givers is provided. A guideline recommendation for a patient is received based on a computer interpretable guideline (CIG). Further, the guideline recommendation is presented to at least one user according to a plurality of alternative approaches for representing the guideline recommendation. At least one of the plurality of alternative approaches visually represent the guideline recommendation.

In accordance with another aspect, a system for presenting guideline recommendations to care givers is provided. The system includes a clinical decision support (CDS) device associated with a user and including at least one processor executing a CDS application. The CDS application is configured to receive a guideline recommendation for a patient based on a computer interpretable guideline (CIG). One of a plurality of alternative approaches for representing the guideline recommendation is selected based on capabilities of the CDS device and/or working conditions of the user. The guideline recommendation is presented to the user according to the selected approach.

One advantage resides in a consistent view of the state of a computer interpretable guideline among different types of devices and different types of applications.

Another advantage resides in a view of the state of a computer interpretable guideline tailored to user interface type.

Another advantage resides in a view of the state of a computer interpretable guideline tailored to working conditions of care givers.

Another advantage resides in a view of the state of a computer interpretable guideline tailored to available screen real-estate.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
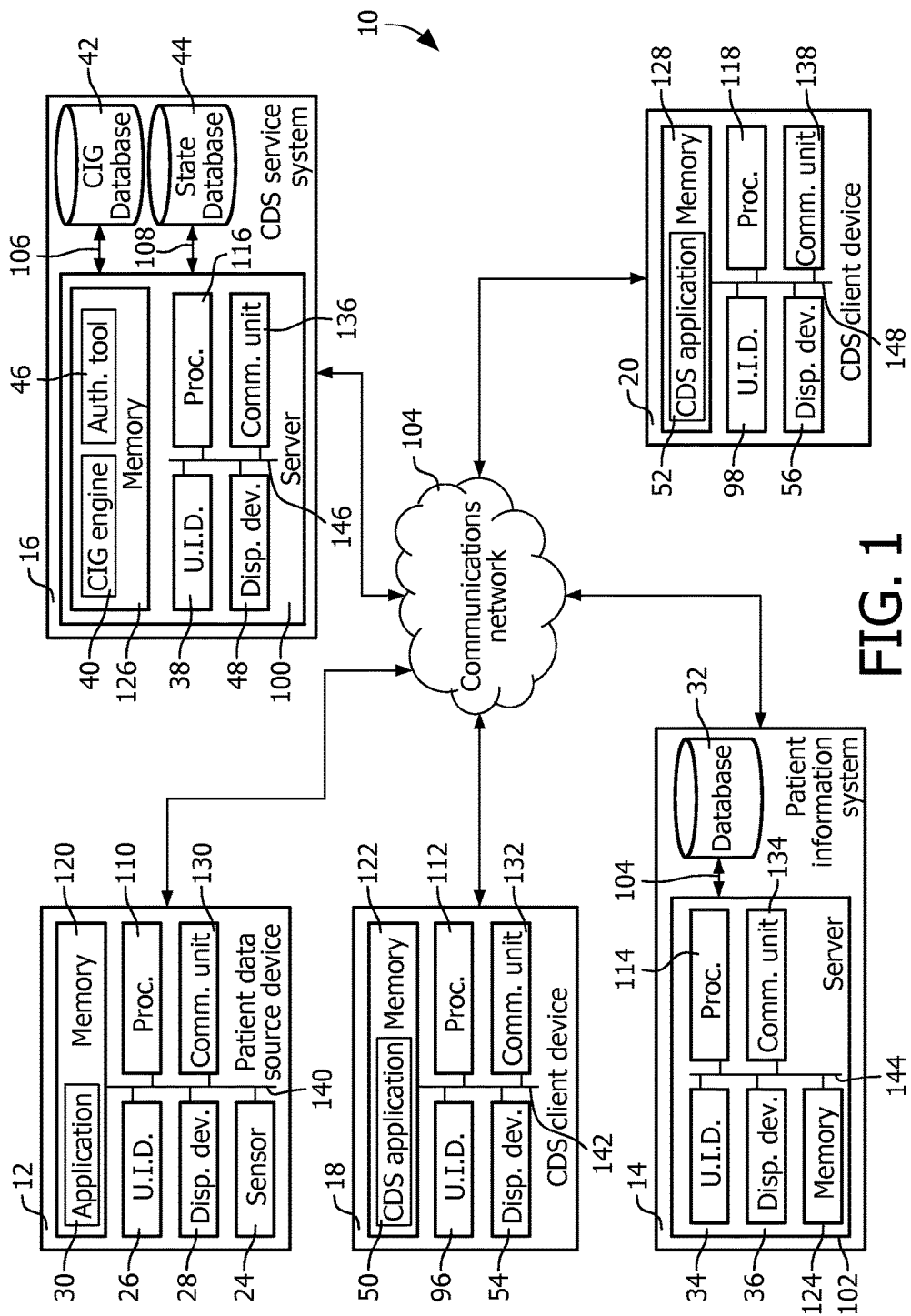
FIG. 1 illustrates a block diagram of an information technology (IT) infrastructure of a medical institution employing a clinical decision support system according to aspects of the present disclosure.

With reference to FIG. 1, an information technology (IT) infrastructure 10 of a medical institution, such as a hospital, includes one or more patient data source devices 12, optionally a patient information system 14, a clinical decision support (CDS) service system 16, and one or more CDS client devices 18, 20. Suitably, the components of the IT infrastructure 10 are interconnected through a communication network 22, such as the Internet, a local area network, a wide area network, a wireless network, or the like.

The patient data source devices 12 generate patient data for corresponding patients. The patient data suitably includes data indicative of one or more physiological parameters, such as heart rate, temperature, blood oxygen saturation, level of consciousness, concern, pain, urine output, and so on. The patient data can also include data indicative of working conditions of care givers and/or care steps (e.g., taking vital sign measurements), performed by care givers. The patient data can be generated automatically and/or manually. As to the former, one or more sensors 24 of the patient data source devices 12, such electrocardiographic (ECG) electrodes, blood pressure sensors, SpO2 sensors, and so on, measuring physiological parameters can be employed. As to the latter, one or more user input devices 26 can be employed, optionally in conjunction with one or more display devices 28 providing users a user interface within which to manually enter the patient data.

Examples of patient data source devices include, but are not limited to, patient monitors, nursing stations, mobile communications devices, patient information systems, and so on. In some embodiments, at least one of the patient data source devices 12 is programmable, each including one or more applications 30 generating patient data. For example, a patient data source device can include an ECG application generating ECG data and a blood pressure application generating blood pressure data.

The patient information system 14 stores patient data from the IT infrastructure 10, such as from the patient data source devices 12, in one or more databases 32. For example, the patient information system 14 can store respiration rate for a patient from one of the patient data source devices 12. In some embodiments, the patient information system 14 also stores patient data from a user input device 34 of the patient information system 14 in the databases 32 and/or allows stored patient data to be viewed on a display device 36 of the patient information system 14. The display device 36 can additionally or alternatively be used to facilitate receipt of data from the user input device 34. Examples of patient information systems include, but are not limited to, electronic medical record systems, departmental systems, and the like.

The CDS service system 16 receives patient data and generates guideline recommendations from the patient data. The guideline recommendations can depend on the role of the recipient of the guideline recommendations. The patient data is typically received from the IT infrastructure 10 (e.g., the patient data source devices 12 and/or the patient information system 14), but can also be received from a user input device 38 of the CDS service system 16. The guideline recommendations are generated by a CIG engine 40 of the CDS service system 16 that applies one or more computer interpretable guidelines (CIGs) in a CIG database 42 of the CDS service system 16 to the received patient data. Guideline recommendations include alerts, notifications, messages, and recommended care steps.

CIGs are computer interpretable representations of clinical guidelines and local care protocols that are derived from the clinical guidelines. Typically, the CIGs are tailored to specific clinical problems, such as diseases. Further, a CIG typically specifies one or more actions, such as alerts, notifications, messages, and care steps, and, where appropriate, a suggested sequence for performance of the actions. Included with the suggested sequence is the requisite logic to advance from one action to another action based on patient data. For example, suppose a CIG includes a first care step to take certain vital sign measurements and a second care step to perform a CT scan of patient's head. The corresponding sequence for the CIG can specify the second care step should be performed if the certain vital sign measurements are irregular.

The CIGs can contain information for presenting guideline recommendations, as discussed below. For example, CIGs can contain information for displaying guideline recommendations as a graph. Nodes represent care steps and links between nodes represent a suggested sequence of care steps. This graph information can be represented in many ways. One approach is to store the (normalized) size and (relative) position of each node, and the (relative) start and end position of each link. An alternative is to store the source and destination node of each link. The presentation information can be generic or specific to different types of clients. As to the former, it falls to the clients to determine how to present guideline recommendations. As to the latter, a CIG can include presentation information for presenting a guideline recommendation in multiple ways, one for each type of client. Hence, it falls on the CDS service system 16 to determine how to present guideline recommendations. The presentation information can be stored using, for example, XML files with an appropriate schema.

The CIG engine 40 typically determines which CIGs to apply to the received patient data of a patient based on clinical problems associated with the patient. As noted above, CIGs are typically tailored to specific clinical problems. The clinical problems associated with a patient can be determined from electronic medical records of the patient in the IT infrastructure 10 (e.g., the patient information system 14) and/or the user input device 38 of the CDS service system 16. The CIG engine 40 can also determine which CIGs to apply to the patient based on a manual selection by, for example, a care giver caring for the patient. Such manual selection can be received from, for example, the IT infrastructure 10 and/or the user input device 38 of the CDS service system 10.

To apply patient data for a patient to a CIG, the CIG engine 40 determines whether an instance of the CIG has been created in a CIG state database 44 for the patient. An instance of a CIG is a copy of a CIG tailored to a particular patient with patient data. Insofar as an instance has not been created in the CIG state database 44, an instance of the CIG is created in the CIG state database 44. Using the instance of the CIG (as created, where applicable), the CIG engine 40 applies the patient data to update the state of the instance of the CIG. For example, the CIG engine 40 changes an instance of a CIG to a different state according to the logic of the CIG in response to receiving patient data indicating completion of an action of the CIG.

The CDS service system 16 optionally includes an authoring tool 46 to allow a user thereof to create or modify CIGs in the CIG database 42. The authoring tool 46 allows the specification of actions, such as care steps, a sequence specifying the relationship between actions, and the requisite logic for transitioning between actions. Further, the authoring tool 46 allows the specification of presentation information. As noted above, presentation information can be globally specified or individually specified for different types of clients. The latter requires prior knowledge of the types of clients. User input is received from the user input device 38, optionally in conjunction with a user interface presented on a display device 48 of the CDS service system 16

The CDS client devices 18, 20 receive guideline recommendations for associated patients from the CIG engine 40, typically over the communication network 22, and present the guideline recommendations to associated users. Further, the CDS client devices 18, 20 can forward guideline recommendations to other ones of the CDS client devices 18, 20. The CDS client devices 18, 20 are programmable devices executing one or more CDS applications 50, 52 to present the guideline recommendations. Alternatively, the CDS client devices 18, 20 are programmable devices executing web browser applications used to access the CDS applications 50, 52 over the communication network 22. In such a case, the CDS applications 50, 52 are run on a web server of the CDS service system 16. In both cases, the CS client devices typically have varying screen real-estate, graphics capabilities, bandwidth, and processing power.

The CDS applications 50, 52 present the guideline recommendations according to several different approaches, typically using a user interface displayed on one or more display devices 54, 56 of the CDS client devices 18, 20. Examples of CDS client devices include pagers, smart phones, patient monitors, tablet PCs, mobile clinical assistants, laptops, workstations, and so on.

Figure 2:
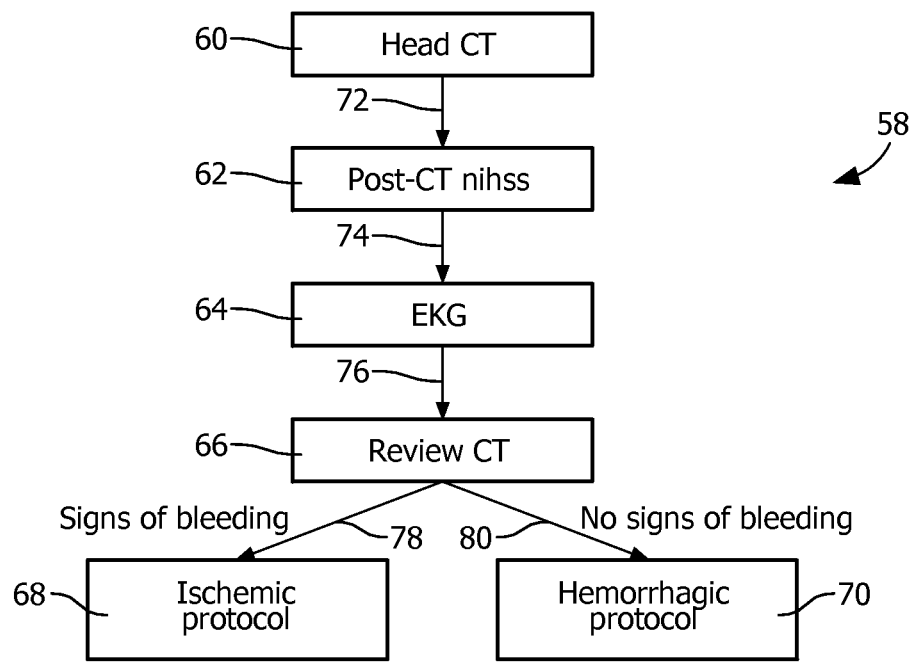
FIG. 2 illustrates a graph-based visualization of a guideline recommendation.

With reference to FIG. 2, one approach the CDS applications 50, 52 can employ for presenting a guideline recommendation is to display at least a part of the corresponding CIG as a graph 58 including one or more nodes 60, 62, 64, 66, 68, 70 and, optionally, one or more links 72, 74, 76, 78, 80. Nodes represent care steps, links between the nodes represent a suggested sequence of care steps, and visualization of the nodes represents status (i.e., different visualizations of nodes correspond to different statuses). Visualization of nodes can be varied using, for example, color, shape, border thickness, and so on. In the illustrated example, background color is employed to represent node status, where node 60 is completed and node 62 is recommended.

By using the graph 58, guideline recommendations are implicit in the patient status. For example, a node indicated as 'active' would be a recommendation to perform the corresponding care step. To adapt the graph 58 to different screen or window sizes, the CDS applications 50, 52 can employ the well-known operations of zooming and scrolling. However, shrinking the graph 58 to show it on a smaller screen or window reduces its readability. Further, scrolling is an extra step that care providers prefer to avoid. Hence, additional approaches for presenting a guideline recommendation are desirable.

Figure 3:
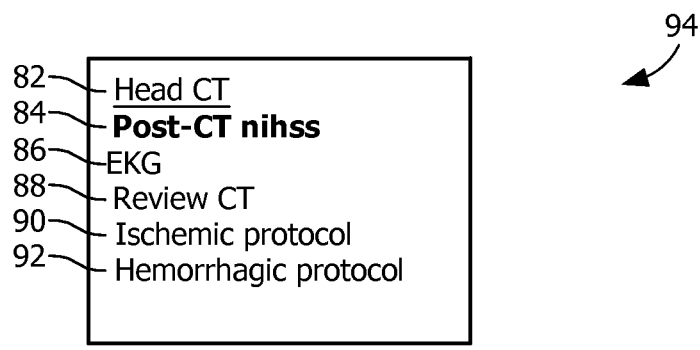
FIG. 3 illustrates a text-based visualization of a guideline recommendation.
Figure 4:
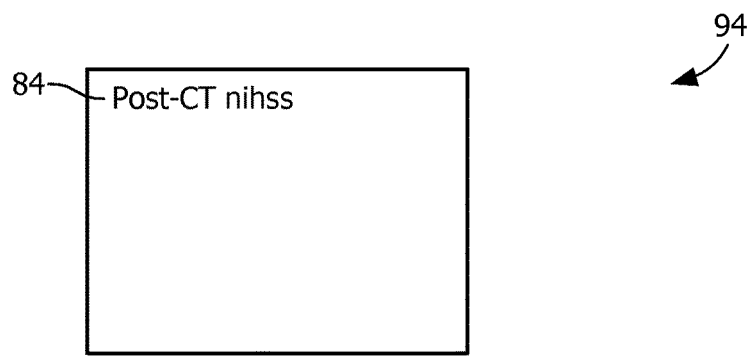
FIG. 4 illustrates a text-based visualization of a guideline recommendation.

With reference to FIGS. 3 & 4, another approach the CDS applications 50, 52 can employ for presenting a guideline recommendation is to display the guideline recommendations as text. For example, as illustrated in FIG. 3, all care steps represented by a CIG graph's nodes can be shown as list items 82, 84, 86, 88, 90, 92 in a list 94, optionally scrollable. Alternatively, rather than showing all care steps in the list 94, only the recommended care steps can be shown, as illustrated in FIG. 4. Further, the list 84 can be a single-column (shown in FIGS. 3 & 4) or a multi-column list. As to the latter, rather than showing all care steps in a single column, there could be multiple columns (e.g., one for currently recommended care steps, one for completed care steps, one for partially completed care steps, and one for care steps that are not (yet) recommended). The user of the CDS applications 50, 52 can optionally select which of the columns to shown by, for example, means of checkboxes or a dropdown menu. List item status can be represented visually using, for example, font color, font size, font weight, underlaying, text shading, and so on. As illustrated in FIG. 3, underlining is employed for completed care steps and bolding is employed for recommended care steps.

Other approaches the CDS applications 50, 52 can employ for presenting a guideline recommendation are to display the guideline recommendations as icons, to display the guideline recommendations as a hybrid of graphs, icons and text, and to play an audio representation of the guideline recommendations. As to the icons, each care step can be represented by an intuitive icon and the state of the care step can be indicated by different visualizations. For example, border color, border thickness, fading, color scale and so on can be used to visualize different statuses. As to the hybrid approach, different combinations of the graph, icon and text based approaches can be employed. For example, lists of icons, equivalent to the above lists of text, could also be used. As to the audio representation, a speech synthesizer can be employed to generate an audio representation of recommended care steps and an audio device can be employed to play the audio representation.

The CDS applications 50, 52 typically determine how to present guideline recommendations based on a number of considerations, discussed below. The determinations can be made using, for example, a simple rules engine applying one or more rules specified by, for example, an operator or developer of the CDS applications 50, 52 or an author of the CIG. The rules suitably embody the following considerations and include the logic to determine which of the above described approaches to employ for displaying guideline recommendations. Further, the CDS applications 50, 52 can dynamically change how to present guideline recommendations in response to events, such as user input events from the user input devices 54, 56 and resizing events. For example, a user of a CDS application can specify how they want guideline recommendations displayed. However, regardless of how a guideline recommendation is presented, the presentation provides a singular, consistent view of the state of care for the instance of the corresponding CIG.

According to one consideration, a guideline recommendation can be shown in different ways on different ones of the CDS client devices 18, 20 depending on the capabilities of the different ones of the CDS client devices 18, 20, such as screen real-estate, graphics capabilities, bandwidth, and processing power. For example, a CDS application can determine whether the corresponding CDS client device includes a display device or an audio device. Insofar as the CDS client device includes only an audio device, guideline recommendations can be presented using the audio approach. Insofar as the CDS client device includes a display device, guideline recommendations can be displayed according to, for example, one or more of the graph, the text, or the icon based approaches depending upon the displaying capabilities of the CDS client device. If the CDS client device includes a display size less than a predetermined size, the text approach would be preferable to the graph approach.

According to another consideration, a guideline recommendation can be displayed differently on a given one of the display devices 54, 56 depending on the allocated screen real estate for presentation of the guideline recommendation. For example, a CDS application can present a guideline recommendation in a resizable window, where the presentation of the guideline recommendation can be tailored to the size of the resizable window. If the resizable window is less than a predetermined size, the text approach would be preferable to the graph approach. Further, as noted above, the presentation of the guideline recommendation can be varied as the size of the resizable window is varied.

According to another consideration, a guideline recommendation can be displayed differently depending upon the design of the user interfaces of the CDS applications 50, 52. For example, a guideline recommendation can be displayed using the text approach for a user interface with a first set of graphical and textual element types and the graph approach for a user interface with a second set of graphical and textual element types.

According to another consideration, a guideline recommendation can be displayed differently depending upon the working conditions of care givers receiving the guideline recommendations. For example, a care giver can be presented with a guideline recommendation using the graph approach when under low pressure (e.g., a low patient load) and presented with the guideline recommendation using the icon approach when under high pressure (e.g., a high patient load). The working conditions of care givers associated with a CDS application can be determined using patient data received from the IT infrastructure 10.

While the CDS applications 50, 52 typically determine how to present guideline recommendations based on the considerations discussed above, the CDS applications 50, 52 can also receive such determinations from the CDS service system 16. As noted above, a CIG can include presentation information for presenting a guideline recommendation in multiple ways, one for each type of CDS application and/or CDS client device. Hence, the CDS applications 50, 52 can merely receive the corresponding presentation information in the CIG and present the guideline recommendations according to the presentation information. In such embodiments, it falls to the CDS service system 16 to properly assess which approach to employ for display guideline recommendations.

To present the guideline recommendations according to the above approaches, the CDS applications 50, 52 employ presentation information in the CIG corresponding to the guideline recommendation. For example, the presentation information can contain information for the graph approach. This information can include the (normalized) size and (relative) position of each node, and the (relative) start and end position of each link. Alternative, this information can include the source and destination node of each link. Additionally or alternatively, the CDS applications 50, 52 employ state information of the CIG corresponding to the guideline recommendation (i.e., the CIG instance of the CIG corresponding to the guideline recommendation). Hence, each CDS application can request this information from the CDS service system 16, or it can have direct access to the CIG database 42 and the CIG instance database 44, typically through the IT infrastructure 10 and/or the CDS service system 16.

Using the presentation information and/or the state information for a guideline recommendation, a CDS application can present the guideline recommendations. For example, the CDS application can render the CIG graph and appropriately visualize node status using the presentation information and the state information, respectively. When the presentation information includes only the source and destination node of each link, the CDS application can employ a graph layout algorithm to determine the relative positioning of the nodes. As another example, the CDS application can render a textual list of care steps and appropriately visualize list item status using the state information. As yet another example, the CDS application can play an audio representation of recommended care step(s) using the state information.

The different visualizations of guideline recommendations, discussed above, can be interactive using one or more user input devices 96, 98 of the CDS client devices 18, 20. For example, a user of a CDS application can select a node of a graph visualization or a list item of a list visualization to change the status of the corresponding care step and/or to bring up an associated data form for entry of patient data. This interactivity can be maintained among different visualizations and among different CDS client devices. For example, changing the status of a care step using a graph based visualization on a first device correspondingly changes the status of the care step as visualized on a second device using a text based visualization. Hence, it is to be appreciated that execution of CIGs is decoupled from visualizing guideline recommendations.

While the CDS applications 50, 52 were shown as independent of the CDS engine 40 (i.e., the CDS engine 40 was part of an external service), it is to be appreciated that the CDS engine 40 can also be part of the CDS applications 50, 52. In that regard, the CDS engine 40 can also be distributed across the CDS applications 50, 52. For example, where the CDS client devices 18, 20 are thick clients, each client can run its own instance of the CIG engine 40, with instances of the CIG engine 40 synchronized over the communication network 22.

Each of the patient information system 14 and the CDS service system 16 include at least one server 100, 102 and at least one database 32, 42, 44. The at least one database 32, 42, 44 can be integrated with the at least one server 100, 102 and/or external to the at least one server 100, 102. As to the former, at least one system bus can be employed for communication. As to the latter, a communication network, such as the communication network 22 of the IT infrastructure 10, and/or at least one system bus 104, 106, 108 can be employed for communication. Communication between the at least one server 100, 102 can be performed over a communication network, such as the communication network 22 of the IT infrastructure 10.

At least some of the components of the IT infrastructure 10 each include at least one processor 110, 112, 114, 116, 118 executing computer executable instructions from at least one memory 120, 122, 124, 126, 128 thereof. Components include the patient data sources 12, at least one server 100, 102, and the CDS client devices 18, 20. The computer executable instructions embody the functionality of the components and include the applications 30 of the patient data sources 12, the CIG engine 40 and/or the authoring tool 46 of the CDS service system 16, and the CDS applications 50, 52 of the CDS client devices 18, 20. Further, at least some of the components each include a communication unit 130, 132, 134, 136, 138 and/or at least one system bus 140, 142, 144, 146, 148. A communications unit provides a corresponding processor with an interface to at least one communication network, such as the communication network 22. A system bus allows the exchange of data between sub-components of the components. Sub-components include processors, memories, sensors, display devices, communication units, and so on.

Figure 5:
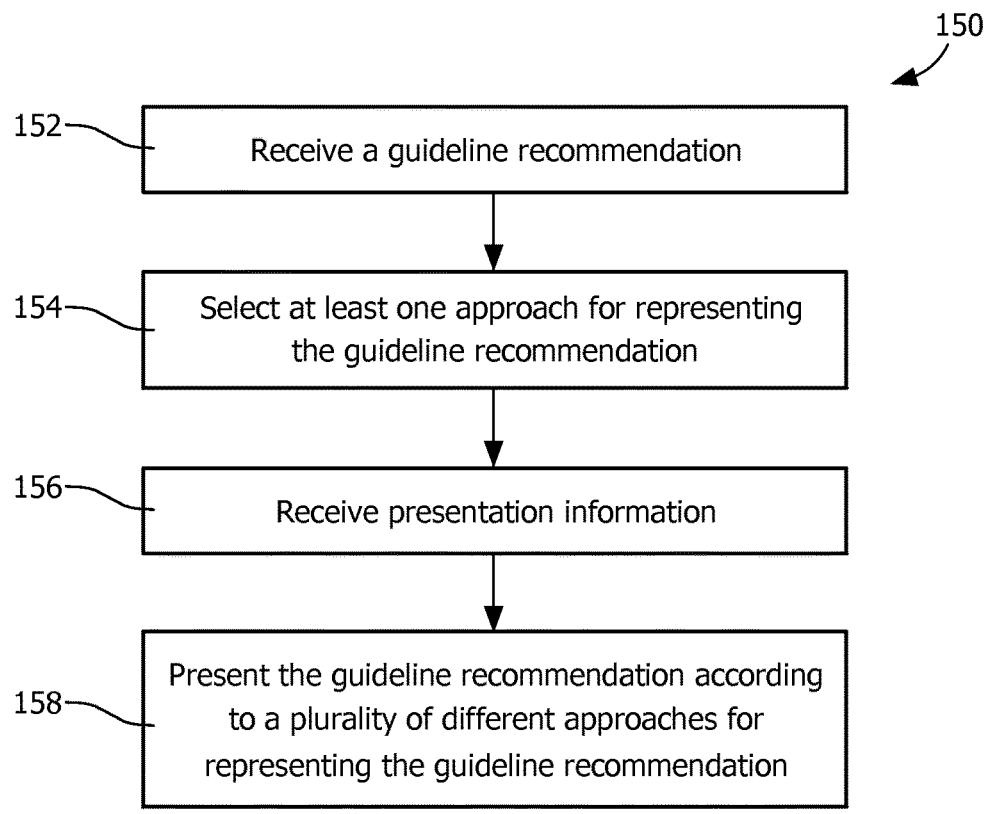
FIG. 5 illustrates a block diagram of a method for presenting guideline recommendations to care givers.

With reference to FIG. 5, a method 150 for presenting guideline recommendations to care givers is provided. The method 150 is suitably performed by the one or more CDS client devices 18, 20, specifically, the one or more CDS applications 50, 52, and allows the presentation of a given guideline recommendation in different ways on different CDS client devices and/or the presentation of a given guideline recommendation in different ways on a single CDS client device.

According to the method 150, a guideline recommendation for a patient based on a computer interpretable guideline (CIG) is received 152, typically from the CIG engine 40. The guideline recommendation can be explicitly received and/or implicitly received. As to the latter, receiving the guideline recommendation includes receiving at least a portion of the CIG and the state for the care steps of the at least a portion of the CIG. As noted above, a CIG includes a plurality of actions, such as care steps, and a sequence for performance of the actions. The state corresponds to where in the sequence the CIG is, including which actions have been started and (partially) completed. Hence, the guideline recommendation is implicit in view of the active care steps.

The method 150 can also include selecting 154 at least one of a plurality of alternative approaches for representing the guideline recommendation. The selection can be based on user input from users associated with the CDS applications 50, 52 and/or based on one or more of capabilities of the CDS client devices 18, 20, working conditions of an associated user (e.g., high work load), type of a user interface of the CDS client devices 18, 20, available screen real-estate of the CDS client devices 18, 20 for displaying the guideline recommendation. The selection 154 can be performed by a single CDS application or spread across a plurality of CDS applications, where the plurality of CDS application present the guideline recommendation (as discussed hereafter) using the respective approach.

The method 150 can also include receiving 156, typically from the CIG engine 40, presentation information indicating at least one of the plurality of alternative approaches and specific to type of the CDS client devices 18, 20 and/or type of the CDS applications 50, 52. As noted above, CIGs can include presentation information for presenting a guideline recommendation in multiple ways, one for each type of client.

Based on the presentation information and/or the selection 154, the guideline recommendation is presented 158 to at least one associated user according to the plurality of alternative approaches. Suitably, at least one of the plurality of alternative approaches uses a user interface of one of the CDS applications 50, 52. For example, one of the CDS applications 50, 52 can present the guideline recommendation using the above described graph approach and another one of the CDS applications 50, 52 can present the guideline recommendation using another one of the above described approaches, such as the audio and/or list approaches. Regardless of the approach employed to present the guideline recommendation, the view of the state of care of the patient as determined by the CIG is consistent.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; a database includes one or more memories; and a display device includes one or more of a LCD display, an LED display, a plasma display, a projection display, a touch screen display, and the like, including 3D-capable versions of these.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system for presenting guideline recommendations to care givers, said system comprising:
at least one display device, each displaying a user interface; and,
at least one processor programmed to:
receive a guideline recommendation for a patient based on a computer interpretable guideline (CIG), wherein the guideline recommendation includes:
state information descriptive of the current state of the CIG, and
presentation information descriptive of at least one visual element, wherein the presentation information includes both data from the state information and meta-data describing how the at least one visual element is to be displayed;
select a presentation approach from a plurality of alternative approaches for representing the guideline recommendation, at least one of the plurality of alternative approaches using the user interface of one of the at least one display device to represent the guideline recommendation, the selection comprising:

determining whether the display device is capable of displaying a first approach wherein a visual presentation is rendered from the presentation information, and based on determining that the display device is not capable of displaying the first approach, displaying a second approach wherein a new presentation is generated based on the state information; and present the guideline recommendation to at least one associated user according to the selected presentation approach.

2. The system according to claim 1, further including:

a clinical decision support (CDS) device associated with at least one user and including at least one processor executing a CDS application, the CDS application configured to:

receive the guideline recommendation;

select one of the plurality of alternative approaches based on capabilities of the CDS device and/or working conditions of the user; and, present the guideline recommendation to the user according to the selected approach.

3. The system according to claim 2, wherein the CDS device further includes a display device displaying a user interface of the CDS application, the CDS application further configured to:

select the one of the plurality of alternative approaches based on type of the user interface and/or available screen real-estate of the display device for displaying the guideline recommendation.

4. The system according to claim 1, further including:

a clinical decision support (CDS) device associated with a user and including at least one processor executing a CDS application, the CDS application configured to:

receive the guideline recommendation and presentation information, the presentation information indicating one of the plurality of alternative approaches and specific to a type of the CDS device and/or a type of the CDS application; and, present the guideline recommendation according to the presentation information.

5. The system according to claim 1, further including:

a first clinical decision support (CDS) device presenting an associated first user with the guideline recommendation according to a first one of the plurality of alternative approaches; and, a second CDS device presenting an associated second user with the guideline recommendation according to a second one of the plurality of alternative approaches.

6. The system according to claim 1, wherein the plurality of alternative approaches include at least a plurality of representing the guideline recommendation: (1) in a single- or multi-column list; (2) in a graph; (3) in a set of one or more icons; (4) as audio; and (5) as a combination of a plurality of (1)-(4).

7. The system according to claim 1, wherein the at least one of the plurality of alternative approaches includes a graph-based approach in which at least a portion of the CIG is displayed as a graph, wherein nodes of the graph correspond to care steps, links between the nodes correspond a sequence for performance of the care steps, and different visualizations of the nodes correspond to different states of the care steps.

8. The system according to claim 1, wherein the at least one of the plurality of alternative approaches includes a list-based approach in which at least a portion of the CIG is displayed as a list, wherein list items of the list correspond to care steps and different visualizations of the list items correspond to different states of the care steps.

9. The system according to claim 1, wherein the at least one display device includes a plurality of display devices, and wherein the plurality of alternative approaches correspondingly use the user interfaces of the plurality of display devices to present the guideline recommendation.

10. The system according to claim 1, wherein the at least one display device includes only a single display device, and wherein the plurality of alternative approaches use the user interface of the single display device to present the guideline recommendation.

11. The system of claim 1, wherein:

the first approach comprises displaying a graph of the CIG and the at least one visual element described by the presentation information includes a node of the graph; and the second approach comprises displaying a textual indication of a current task indicated by the state information.

12. A method for presenting guideline recommendations to care givers, said method comprising:

receiving a guideline recommendation for a patient based on a computer interpretable guideline (CIG) wherein the guideline recommendation includes:

state information descriptive of the current state of the CIG, and presentation information descriptive of at least one visual element, wherein the presentation information includes both data from the state information and meta-data describing how the at least one visual element is to be displayed;

selecting a presentation approach from a plurality of alternative approaches for representing the guideline recommendation, at least one of the plurality of alternative approaches visually representing the guideline recommendation, the selection comprising:

determining whether the display device is capable of displaying a first approach wherein a visual presentation is rendered from the presentation information, and based on determining that the display device is not capable of displaying the first approach, displaying a second approach wherein a new presentation is generated based on the state information; and presenting the guideline recommendation to at least one associated user according to the selected presentation approach.

13. The method according to claim 12, further including:

selecting by a CDS device one of the plurality of alternative approaches based on one or more of capabilities of the CDS device, working conditions of an associated user, type of a user interface of the CDS device, and available screen real-estate of the CDS device for displaying the guideline recommendation; and, presenting the guideline recommendation to the associated user according to the selected approach.

14. The method according to claim 12, further including:

receiving, by a CDS device executing a CDS application, presentation information indicating one of the plurality of alternative approaches and specific to a type of the CDS device and/or a type of the CDS application; and, presenting the guideline recommendation according to the presentation information.

15. The method according to claim 12, further including:
presenting by a first clinical decision support (CDS) device the guideline recommendation according to a first one of the plurality of alternative approaches; and,
presenting by a second CDS device the guideline recommendation according to a second one of the plurality of alternative approaches.

16. The method according to claim 12, wherein the at least one of the plurality of alternative approaches includes a graph-based approach in which at least a portion of the CIG is displayed as a graph, wherein nodes of the graph correspond to care steps, links between the nodes correspond a sequence for performance of the care steps, and different visualizations of the nodes correspond to different states of the care steps.

17. The method according to claim 12, wherein the at least one of the plurality of alternative approaches includes a list-based approach in which at least a portion of the CIG is displayed as a list, wherein list items of the list correspond to care steps and different visualizations of the list items correspond to different states of the care steps.

18. The method of claim 12 wherein:
the first approach comprises displaying a graph of the CIG and the at least one visual element described by the presentation information includes a node of the graph; and
the second approach comprises displaying a textual indication of a current task indicated by the state information.

19. A non-transitory computer readable medium encoded with instructions for execution by a processor for presenting guideline recommendations to care givers, the non-transitory computer readable medium comprising:
instructions for receiving a guideline recommendation for a patient based on a computer interpretable guideline (CIG) wherein the guideline recommendation includes:
state information descriptive of the current state of the CIG, and
presentation information descriptive of at least one visual element, wherein the presentation information includes both data from the state information and meta-data describing how the at least one visual element is to be displayed;
instructions for selecting a presentation approach from a plurality of alternative approaches for representing the guideline recommendation, at least one of the plurality of alternative approaches visually representing the guideline recommendation, the selection comprising:
determining whether the display device is capable of displaying a first approach wherein a visual presentation is rendered from the presentation information, and
based on determining that the display device is not capable of displaying the first approach, displaying a second approach wherein a new presentation is generated based on the state information; and
instructions for presenting the guideline recommendation to at least one associated user according to the selected presentation approach.

20. The non-transitory computer readable medium of claim 19, wherein:
the first approach comprises displaying a graph of the CIG and the at least one visual element described by the presentation information includes a node of the graph; and
the second approach comprises displaying a textual indication of a current task indicated by the state information.

* * * * *